(12) United States Patent
Allard et al.

(10) Patent No.: US 7,374,582 B2
(45) Date of Patent: May 20, 2008

(54) CONDITIONING CREAM COLOR BASE HAVING IMPROVED COLOR DEPOSITION PROPERTIES

(75) Inventors: Delphine Allard, Westfield, NJ (US); Jean-Marc Ascione, Paris (FR); Jean-Marc Dumontier, Fanwood, NJ (US)

(73) Assignee: L'Oreal, Paris (FR)

( * ) Notice: Subject to any disclaimer, the term of this patent is extended or adjusted under 35 U.S.C. 154(b) by 204 days.

(21) Appl. No.: 11/416,056

(22) Filed: May 2, 2006

(65) Prior Publication Data

US 2007/0256254 A1 Nov. 8, 2007

(51) Int. Cl.
*A61Q 5/10* (2006.01)

(52) U.S. Cl. .................. 8/405; 8/406; 8/408; 8/410; 8/411; 8/412; 8/435; 8/525; 8/552; 8/554; 8/586; 8/594; 8/604

(58) Field of Classification Search ............ 8/405, 8/406, 410, 411, 412, 435, 525, 552, 554, 8/586, 594, 604
See application file for complete search history.

(56) References Cited

U.S. PATENT DOCUMENTS

| | | | |
|---|---|---|---|
| 2,528,378 | A | 10/1950 | Mannheimer |
| 2,781,354 | A | 2/1957 | Mannheimer |
| 4,027,020 | A | 5/1977 | Green et al. |
| 4,185,087 | A | 1/1980 | Morlino |
| 5,061,289 | A | 10/1991 | Clausen et al. |
| 5,380,340 | A | 1/1995 | Neunhoeffer et al. |
| 5,534,267 | A | 7/1996 | Neunhoeffer et al. |
| 5,766,576 | A | 6/1998 | Lowe et al. |
| 6,099,592 | A | 8/2000 | Vidal et al. |
| 2003/0009834 | A1 | 1/2003 | Ascione et al. |
| 2004/0205902 | A1* | 10/2004 | Cottard et al. ............ 8/405 |
| 2005/0125912 | A1 | 6/2005 | Desenne et al. |

FOREIGN PATENT DOCUMENTS

| | | |
|---|---|---|
| DE | 3843892 | 6/1990 |
| DE | 4133957 | 4/1993 |
| DE | 19543988 | 5/1997 |
| FR | 1492597 | 8/1967 |
| FR | 2733749 | 11/1996 |
| GB | 1026978 | 4/1966 |
| GB | 1153196 | 5/1969 |
| WO | WO-9408969 | 4/1994 |
| WO | WO-9408970 | 4/1994 |
| WO | WO-03/017957 | 3/2003 |

OTHER PUBLICATIONS

M.R.Porter, Handbook of Surfactants, 1991, pp. 116-178, published by Blackie & Son (Glasgow and London).
John A. Wenninger, G. N. Mcewen, International Cosmetic Ingredient Dictionary, 1993, 5th edition, published by The Cosmetic, Toiletry, and Fragrance Association, Washington D.C. USA.
John A. Wenninger, G. N. Mcewen, Joanne M. Nikitakis, International Cosmetic Ingredient Dictionary, 1991, 4th edition, published by The Cosmetic, Toiletry, and Fragrance Association, Washington D.C. USA.
Norman P. Estrin, Patricia Crosley, Charles Haynes, International Cosmetic Ingredient Dictionary, 1982, 3rd edition, published by The Cosmetic, Toiletry, and Fragrance Association, Washington D.C. USA.

* cited by examiner

*Primary Examiner*—Eisa B Elhilo
(74) *Attorney, Agent, or Firm*—Maria Luisa Balasta; Francois Maniere; Steven Trzaska

(57) ABSTRACT

The present invention is directed to a process and composition for dyeing hair, the composition containing: (a) greater than about 10% by weight, based on the weight of the composition, of at least one fatty acid alkanolamide; (b) at least one $C_6$-$C_{36}$ dicarboxylic acid; (c) at least one water soluble base capable of reacting with (b) to form a soap; (d) at least one conditioning polymer; (e) at least one oxidation dye; and (f) at least one oxidizing agent, wherein the composition is in cream form.

27 Claims, No Drawings

CONDITIONING CREAM COLOR BASE HAVING IMPROVED COLOR DEPOSITION PROPERTIES

BACKGROUND OF THE INVENTION

Disclosed herein is a composition, in cream form, for the oxidation dyeing of keratin fibers, for example human keratin fibers, such as the hair.

It is a known practice to dye keratin fibers, such as human hair, with dye compositions comprising oxidation dye precursors, generally known as "oxidation bases", such as ortho- and para-phenylenediamines, ortho- and para-aminophenols, and heterocyclic bases.

Oxidation dye precursors are compounds that are initially uncolored or only weakly colored, which develop their dyeing power on the hair in the presence of oxidizing agents, leading to the formation of colored compounds. The formation of these colored compounds may result either from an oxidative condensation of the oxidation bases with themselves or from an oxidative condensation of the oxidation bases with coloration modifiers, or "couplers", which may be present in the dye compositions used in oxidation dyeing and may be represented for example by meta-phenylenediamines, meta-aminophenols, meta-diphenols, and certain heterocyclic compounds.

The variety of molecules used, which comprise on the one hand the oxidation bases and on the other hand the couplers, may allow a wide range of colors to be obtained.

BRIEF SUMMARY OF THE INVENTION

The present invention is directed to a composition for the oxidation dyeing of keratin fibers, such as the hair, comprising, in a medium suitable for dyeing:
a) greater than 10% by weight of at least one fatty acid alkanolamide;
b) at least one $C_6$-$C_{36}$ dicarboxylic acid;
c) at least one water soluble base capable of reacting with (b) to form a soap;
d) at least one conditioning polymer; and
e) at least one oxidation dye.

The present invention is also directed to a ready-to-use hair dyeing composition containing:
a) greater than 10% by weight of at least one fatty acid alkanolamide;
b) at least one $C_{16}$-$C_{36}$ dicarboxylic acid;
c) at least one water soluble base capable of reacting with (b) to form a soap;
d) at least one conditioning polymer;
e) at least one oxidation dye; and
f) at least one oxidizing agent.

The present invention is also directed to a process for dyeing keratin fibers, such as hair, by contacting the keratin fibers with the above-disclosed ready-to-use dyeing composition.

The present invention is also directed to a multi-compartment kit for the oxidation dyeing of keratin fibers, such as hair, the kit containing:

a) a first compartment comprising: i) greater than 10% by weight of at least one fatty acid alkanolamide; ii) at least one $C_6$-$C_{36}$ dicarboxylic acid; iii) at least one water soluble base capable of reacting with (b) to form a soap; iv) at least one conditioning polymer; and v) at least one oxidation dye, and b) a second compartment comprising at least one oxidizing agent.

It has been surprisingly discovered that by combining the above-disclosed ingredients, a dyeing composition, in cream form, may be formulated yielding excellent color deposition on hair treated therewith, while at the same time imparting desirable conditioning properties.

DETAILED DESCRIPTION OF THE INVENTION

Other than in the operating examples, or where otherwise indicated, all numbers expressing quantities of ingredients and/or reaction conditions are to be understood as being modified in all instances by the term "about".

As used herein, the expression "ready-to-use dyeing composition" means the composition intended for application as it is to the keratin fibers; that is to say, the composition may be stored as it is before use or may result from mixing of at least two compositions.

Suitable fatty acid alkanolamides include those formed by reacting an alkanolamine and a $C_6$-$C_{36}$ fatty acid. Examples thereof include, but are not limited to:
oleic acid diethanolamide, such as the amide sold under the trade name MEXANYL® GT by the company Chimex;
myristic acid monoethanolamide, such as the amide sold under the trade name COMPERLAN® MM by the company Cognis;
soya fatty acids diethanolamide, such as the amide sold under the trade name COMPERLAN® VOD by the company Cognis;
stearic acid ethanolamide, such as the amide sold under the trade name MONAMID® S by the company Uniqema;
oleic acid monoisopropanolamide, such as the amide sold under the trade name WITCAMIDE® 61 by the company Witco;
linoleic acid diethanolamide, such as the amide sold under the trade name PURTON® SFD by the company Zschimmer Schwarz;
stearic acid monoethanolamide, such as the amide sold under the trade name MONAMID® 972 by the company ICI/Uniqema;
behenic acid monoethanolamide, such as the amide sold under the trade name INCROMIDE® BEM from Croda;
isostearic acid monoisopropanolamide, such as the amide sold under the trade name WITCAMIDE® SPA by the company Witco;
erucic acid diethanolamide, such as the amide sold by the company Stearineries Dubois;
ricinoleic acid monoethanolamide, such as the amide sold by the company Stearineries Dubois;
coconut isopropanolamide, such as the amide sold by the company Cognis and
coconut acid monoethanolamide, such as the amide sold under the trade name MONAMID CMA by the company Uniquema.

The fatty acid alkanolamides may be either monoalkanolamides or dialkanolamides, and may have a $C_{2-3}$ hydroxyalkyl group. Examples thereof include, but are not limited to, oleic diethanolamide, palm kernel fatty acid diethanolamide, coconut fatty acid diethanolamide, lauric diethanolamide, polyoxyethylene coconut fatty acid monoethanolamide, coconut fatty acid monoethanolamide, lauric isopropanolamide and lauric monoethanolamide.

Preferred fatty acid alkanolamides include Cocamide MEA (Coco monoethanolamide) and Stearamide MEA (Stearic acid monoethanolamide).

The at least one fatty acid alkanolamide may be present in the composition in an amount greater than 10% by weight; greater than 15% by weight; greater than 20% by weight, all weights being based on the total weight of the composition. The at least one $C_6$-$C_{36}$ dicarboxylic acid will typically be present in the composition of the invention in amounts of from 0.1 to 15% by weight; from 0.5 to 12% by weight; from 1 to 8% by weight, all weights being based on the weight of the composition. Its purpose is to facilitate color deposition onto keratin fibers treated therewith.

A particularly preferred $C_{6-36}$ dicarboxylic acid for use in the present invention is dilinoleic acid.

Any water-soluble base capable of reacting with the fatty acid alkanolamide may be employed. Examples thereof include, but are not limited to, alkaline hydroxides, alkaline metal hydroxides, amines, alkanolamines, and the like.

Preferred water-soluble bases include alkanolamines such as mono-, di- and tri-alkanolamines. Examples thereof include, but are not limited to, mono-, di- and tri-ethanolamines.

The water-soluble base will typically be present in the composition of the invention in an amount of from 0.01 to 5% by weight; from 0.1 to 3% by weight; from 0.5 to 2% by weight, all weights being based on the weight of the composition.

The at least one oxidation dye that may be used according to certain embodiments may be chosen from oxidation bases and couplers.

The composition disclosed herein may comprise at least one oxidation base.

The oxidation bases that may be used in the context of certain embodiments may be chosen from those conventionally used in oxidation dyeing, and among which mention may be made of ortho- and para-phenylenediamines, double bases, ortho- and para-aminophenols, heterocyclic bases, and the acid addition salts thereof.

Among the para-phenylenediamines, mention may be made of para-phenylenediamine, 2-methyl-para-phenylenediamine, 1-(N-ethyl-N'-β-hydroxyethyl)-amino-4-aminobenzene, 1-N,N'-bis(β-hydroxyethyl) amino-4-aminobenzene, 1-N,N'-bis(β,γ-dihydroxypropyl) amino-4-aminobenzene, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, 4-amino-N,N-diethyl-2-methylaniline, N,N-bis(β-hydroxyethyl)-para-phenylenediamine, 4-amino-N,N-bis(β-hydroxyethyl)-3-methylaniline, 4-amino-3-chloro-N,N-bis(β-hydroxyethyl)aniline, 4-amino-N-ethyl-N-carbamylmethyl-aniline, 4-amino-3-methyl-N-ethyl-N-carbamylmethyl-aniline, 4-amino-N-ethyl-N-(β-piperidinoethyl) aniline, 4-amino-3-methyl-N-ethyl-N-(β-piperidinoethyl) aniline, 4-amino-N-ethyl-N-(β-morpholinoethyl) aniline, 4-amino-3-methyl-N-ethyl-N-(β-morpholinoethyl) aniline, 4-amino-ethyl-N-(β-acetylaminoethyl) aniline, 4-amino-N-(β-methoxyethyl)aniline, 4-amino-3-methyl-N-ethyl-N-(β-acetylaminoethyl)aniline, 4-amino-N-ethyl-N-(β-mesylaminoethyl)aniline, 4-amino-3-methyl-N-ethyl-N-(β-mesylaminoethyl) aniline, 4-amino-N-ethyl-N-(β-sulphoethyl)aniline, 4-amino-3-methyl-N-ethyl-N-(β-sulphoethyl)aniline, N-[4'-(amino)phenyl]morpholine, N[4'-(amino)phenyl]piperidine, N-(4'-aminophenyl)-para-phenylenediamine, N-phenyl-para-phenylenediamine, 2-fluoro-para-phenylenediamine, 2-carboxy-para-phenylenediamine, 2-sulpho-para-phenylenediamine, 2-isopropyl-para-phenylenediamine, N-(β hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, 2-β-hydroxyethyloxy-para-phenylenediamine, 2-β-acetylaminoethyloxy-para-phenylenediamine, N-β-methoxyethyl-para-phenylenediamine, para-toluoylenediamine, 2-n-propyl-para-phenylenediamine, 1,β-methoxyethylamino-4-aminobenzene, 4-aminophenyl 1-(3-hydroxy)pyrrolidone, and acid addition salts thereof.

Among the ortho-phenylenediamines, mention may be made of N1-(2-Hydroxyethyl)-4-Nitro-o-Phenylenediamine, 4-Methyl-o-Phenylenediamine, and 4-Nitro-o-Phenylenediamine and acid addition salts thereof.

As used herein, the term double bases means compounds comprising at least two aromatic nuclei having at least one of amino and hydroxyl groups.

Among the double bases that can be used as oxidation bases in the dye compositions disclosed herein, mention may be made of amino, mono($C_1$-$C_4$) alkylamino, di($C_1$-$C_4$) alkylamino, tri($C_1$-$C_4$) alkylamino, monohydroxy($C_1$-$C_4$) alkylamino, imidazolinium, and ammonium radicals. Mention may also be made of N,N'-bis-(β-hydroxyethyl)-N,N'-bis(4'-aminophenyl)-1,3-diaminopropanol, N,N'-bis(β-hydroxyethyl)-N,N'-bis(4'-aminophenyl) ethylenediamine, N,N'-bis(4-aminophenyl)tetra-methylenediamine, N,N'-bis(β-hydroxyethyl)-N,N'-bis-(4-aminophenyl) tetramethylenediamine, N,N'-bis(4-methylaminophenyl) tetramethylenediamine, N,N'-bis(ethyl)-N,N'-bis(4'-amino-3'-methylphenyl) ethylenediamine, 1,8-bis(2,5-diaminophenoxy)-3,5-dioxaoctane, and the acid addition salts thereof.

Among the para-aminophenols, mention may be made of para-aminophenol, 4-amino-3-methylphenol, 4-amino-3-fluorophenol, 4-amino-3-hydroxymethylphenol, 4-amino-2-methylphenol, 4-amino-2-hydroxymethyl phenol, 4-amino-2-methoxymethylphenol, 4-amino-2-aminomethylphenol, 4-amino-2-(β-hydroxyethylaminomethyl) phenol, N-methyl-para-aminophenol, and the acid addition salts thereof.

The ortho-aminophenols that may be used as oxidation bases in the context of certain embodiments may be chosen from 2-aminophenol, 2-amino-1-hydroxy-5-methylbenzene, 2-amino-1-hydroxy-6-methylbenzene, 5-acetamido-2-aminophenol, and the acid addition salts thereof.

Among the heterocyclic bases that can be used as oxidation bases in the dye compositions in accordance with certain embodiments, mention may be made of pyridine derivatives, pyrimidine derivatives, pyrazole derivatives, pyrazolinone derivatives, and the acid addition salts thereof.

Among the pyridine derivatives, mention may be made of the compounds described, for example, in patents GB 1,026,978 and GB 1,153,196, as well as the compounds 2,5-diaminopyridine, 2-(4-methoxyphenyl)amino-3-aminopyridine, 2,3-diamino-6-methoxypyridine, 2-(β-methoxyethyl) amino-3-amino-6 methoxypyridine, 3,4-diaminopyridine, and the acid addition salts thereof.

Among the pyrazole and pyrazolinone derivatives, mention may be made of the compounds described in patents DE 3,843,892, DE 4,133,957 and patent applications WO 94/08969, WO 94/08970, FR-A-2,733,749, and DE 195 43 988, such as 4,5-diamino-1-methyl-pyrazole, 3,4-diaminopyrazole, 4,5-diamino-1-(4'-chlorobenzyl) pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethyl-pyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl) amino-1-methylpyrazole, 2-(4,5-diamino-1H-pyrazol-1-yl), $H_2SO_4$, 2,3-diamino-6,7-dihydro-1H,5H-pyrazolo[1,2-z] pyrazol-1-one, 1-methyl-3-phenyl-2-pyrazolinone, and the acid addition salts thereof;

The oxidation bases may be employed in amounts ranging from 0.0001% to 12% by weight; from 0.001% to 8% by weight, all weights being based on the total weight of the composition.

The couplers that may be used in the dyeing method disclosed herein include those conventionally used in oxidation dye compositions, that is to say meta-aminophenols, meta-phenylenediamines and meta-diphenols, naphthols and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines, and the acid addition salts thereof.

These couplers may be chosen, for example, from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino 1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole, 2,6-dimethylpyrazolo[1,5-b]-1,2,4-triazole, 6-methylpyrazolo[1,5-a]-benzimidazole, and the acid addition salts thereof.

When they are present, these couplers may be present in amounts ranging from 0.0001% to 12% by weight; from 0.001% to 8% by weight, all weights being based on the total weight of the composition.

In general, the acid addition salts of the oxidation bases and couplers may be chosen from hydrochlorides, hydrobromides, sulphates, tartrates, lactates, and acetates.

The composition disclosed herein may also comprise at least one direct dye, in addition to the at least one oxidation dye defined above, in order to enrich the shades with glints. This at least one direct dye may be chosen from neutral, cationic, and anionic nitro dyes, azo dyes, and anthraquinone dyes, and may be present in amounts ranging from 0.001% to 20% by weight; from 0.01% to 10% by weight, all weights being based on the total weight of the composition.

The conditioning polymers employed by the present invention are typically chosen from polymers containing primary, secondary, tertiary and/or quaternary amine groups, forming part of the polymer chain or linked directly to the latter, and having a molecular weight of between 500 and approximately 5,000,000, and preferably between 1000 and 3,000,000.

Among these polymers, there may be mentioned, more especially, quaternized proteins, polymers of the polyamine, polyaminoamide or poly(quaternary ammonium) family and cationic polysiloxanes.

A. The quaternized proteins are, in particular, chemically modified polypeptides bearing quaternary ammonium groups at the end of the chain or grafted onto the latter. Among these proteins, there may be mentioned, in particular:

1) collagen hydrolysates bearing triethylammonium groups, such as the products sold by the company MAYBROOK under the name "QUAT-PRO E" and designated in the CTFA Dictionary "Triethonium Hydrolyzed Collagen Ethosulfate";
2) collagen hydrolysates bearing trimethylammonium and dimethylstearylammonium chloride groups, sold by the company MAYBROOK under the name "QUAT-PRO S" and designated in the CTFA Dictionary "Steartrimonium Hydrolyzed Collagen";
3) animal protein hydrolysates bearing dimethylbenzylammonium groups, such as the products sold by the company CRODA under the name "CROTEIN BTA" and designated in the CTFA Dictionary "Benzyltrimonium Hydrolyzed Animal Protein";
4) protein hydrolysates bearing on the polypeptide chain quaternary ammonium groups containing at least one alkyl radical having from 1 to 18 carbon atoms. Among these protein hydrolysates, there may be mentioned, inter alia:
5) CROQUAT L, in which the polypeptide chain has an average molecular weight of approximately 2500 and in which the quaternary ammonium group contains a $C_{12}$ alkyl group;
6) CROQUAT M, in which the polypeptide chain has an average molecular weight of approximately 2500 and in which the quaternary ammonium group contains a $C_{10}$-$C_{18}$ alkyl group;
7) CROQUAT S, in, which the polypeptide chain has an average molecular weight of approximately 2700 and in which the quaternary ammonium group contains a $C_{18}$ alkyl group;
8) CROQUAT Q, in which the polypeptide chain has an average molecular weight of the order of 12,000 and in which the quaternary ammonium group contains at least one alkyl group having from 1 to 18 carbon atoms;
9) a soybean quaternized vegetable protein sold under the name CROQUAT SOYA.

These various products are sold by the company CRODA.
10) a quaternized protein resulting from the condensation of cocamidopropyldimethylamine with a hydrolyzed animal protein, designated in the CTFA Dictionary, 1991 edition, Quaternium 76 Hydrolysed Collagen, sold by the company INOLEX under the name LEXEIN QX 3000.

B. Among the polyamine, polyaminoamide or poly(quaternary ammonium) family of polymers, there may be mentioned:
1) Vinylpyrrolidone/dialkylaminoalkyl acrylate or methacrylate copolymers, quaternized or otherwise, such as the products sold by the company GAF CORPORA- TION under the name "GAFQUAT", for example "GAFQUAT 734 or 755", or alternatively the products designated "COPOLYMER 845, 958 and 937".

2) The cellulose ether derivatives containing quaternary ammonium groups described in French Patent 1,492,597, and especially the polymers marketed by the company UNION CARBIDE CORPORATION under the names "JR" (JR 400, JR 125, JR 30M) or "LR" (LR 400, LR 30M). The polymers are also defined in the CTFA Dictionary as quaternary ammonium derivatives of hydroxyethylcellulose subjected to reaction with an epoxide substituted with a trimethylammonium group.

3) Cationic cellulose derivatives such as cellulose copolymers or cellulose derivatives grafted with a water-soluble quaternary ammonium monomer such as, for example hydroxyalkylcelluloses such as hydroxymethyl-, hydroxyethyl- or hydroxypropylcellulose grafted with a methacryloylethyltrimethylammonium, methacrylamidopropyltrimethylammonium or dimethyldiallylammonium salt.

Marketed products corresponding to this definition are, more especially, the products sold by the company NATIONAL STARCH under the names "CELQUAT L 200" and "CELQUAT H 100".

4) The quaternized polysaccharides marketed under the name "JAGUAR C 13 S", sold by the company MEYHALL.

5) Polymers consisting of piperazinyl units and divalent alkylene or hydroxyalkylene radicals having unbranched or branched chains optionally interrupted by oxygen, sulfur or nitrogen atoms or by aromatic or heterocyclic ring-systems, as well as the oxidation and/or quaternization products of these polymers.

6) Water-soluble polyaminoamides prepared, in particular, by polycondensation of an acid compound with a polyamine. These polyaminoamides may be crosslinked with an epihalohydrin, a diepoxide, a dianhydride, an unsaturated anhydride, a bis-unsaturated derivative, a bis-halohydrin, a bis-azetidinium compound, a bis-haloacyldiamine or a bis(alkyl halide), or alternatively with an oligomer resulting from the reaction of a bi-functional compound which is reactive towards a bis-halohydrin, a bis-azetidinium compound, a bis-haloacyldiamine, a bis(alkyl halide), an epihalohydrin, a diepoxide or a bis-unsaturated derivative; the crosslinking agent being used in proportions ranging from 0.025 to 0.35 mol per amide group of the polyaminoamide.

These polyaminopolyamides may be alkylated or, if they contain one or more tertiary amine functions, quaternized.

7) Polyaminoamide derivatives resulting from the condensation of polyalkylenepolyamines with polycarboxylic acids followed by an alkylation with bi-functional agents. There may be mentioned, for example, adipic acid/dialkylaminohydroxyalkyl/dialkylenetriamine polymers in which the alkyl radical contains from 1 to 4 carbon atoms and preferably denotes methyl, ethyl or propyl.

Among these derivatives, there may be mentioned, more especially, the adipic acid/dimethylaminohydroxypropyl/diethylenetriamine polymers sold by the company SANDOZ under the name "CARTARETINE F, F4 or F8".

8) Polymers obtained by reaction of a polyalkylenepolyamine containing two primary amine groups and at least one secondary amine group with a dicarboxylic acid chosen from diglycolic acid and saturated aliphatic dicarboxylic acids having from 3 to 8 carbon atoms. The mole ratio of the polyalkylenepolyamine to the dicarboxylic acid is between 0.8:1 and 1.4:1; the polyaminoamide resulting therefrom being reacted with epichlorohydrin in a mole ratio of epichlorohydrin relative to the secondary amine group of the polyaminoamide of between 0.5:1 and 1.8:1.

Polymers of this type are, in particular, marketed by the company HERCULES INCORPORATED under the name "HERCOSETT 57", or alternatively by the company HERCULES under the name "PD 170" or "DELSETTE 101" in the case of the adipic acid/epoxypropyl/diethylenetriamine copolymer.

9) Cyclopolymers having a molecular weight of 20,000 to 3,000,000 such as, for example, the homopolymer of dimethyldiallylammonium chloride sold by the company MERCK under the name "MERQUAT 100", having a molecular weight of less than 100,000, and the copolymer of dimethyldiallylammonium chloride and acrylamide having a molecular weight above 500,000 and sold under the name "MERQUAT 550".

10) The poly(quaternary ammonium) polymers such as those described in U.S. Pat. No. 4,027,020.

11) The poly(quaternary ammonium) polymers such as the products "MIRAPOL A 15", "MIRAPOL AD1", "MIRAPOL AZ1l" and "MIRAPOL 175" sold by the company MIRANOL.

12) Homopolymers or copolymers derived from acrylic or methacrylic esters or amides such as the copolymer of acrylamide and dimethylaminoethyl methacrylate quaternized with dimethyl sulfate and sold by the company HERCULES under the name "HERCOFLOC", the copolymer of acrylamide and methacryloyloxyethyltrimethylammonium chloride sold by the company CIBA GEIGYC under the name "BINA QAT P100", or alternatively the poly-(methacrylamidopropyltrimethylammonium chloride) sold by the company TEXACO CHEMICALS under the name "POLYMAPTAC", and the methacryloyloxyethyltrimethylammonium methosulfate and its copolymer with acrylamide which are sold by the company HERCULES under the name "RETEN".

13) Quaternary polymers of vinylpyrrolidone and of vinylimidazole, such as, for example, the products marketed by the company BASF under the names "LUVIQUAT FC 905, FC 550 and FC 370".

14) Polyamines such as Polyquart H sold by HENKEL, listed under the reference name "POLYETHYLENE GLYCOL (15) TALLOW POLYAMINE" in the CTFA Dictionary.

Other conditioning polymers which are useable according to the invention are polyalkylenimines, especially polyethylenimines, polymers containing vinylpyridine or vinylpyridinium units, condensates of polyamines and epichlorohydrin, quaternary polyureylenes and chitin derivatives. The cationic polysiloxanes such as those described in U.S. Pat. No. 4,185,087.

The conditioning polymers may also be chosen from amphoteric polymers, such as amphoteric polymers derived from chitosan or copolymers of diallyldialkylammonium and an anionic monomer.

Preferred polymers are, inter alia, polymers containing alkyl groups chosen from groups having 1 to 4 carbon atoms, and more especially methyl and ethyl groups.

Among these polymers, copolymers of dimethyldiallylammonium or diethyldiallylammonium chloride and acrylic acid are especially preferred.

As especially preferred products, there may be mentioned the polymer sold by the company CALGON under the name "MERQUAT 280" in the form of an aqueous solution containing 35% of active substance, this polymer being a copolymer of diallyldimethylammonium chloride and acrylic acid in the proportions 80:20, the viscosity in a module 4 Brookfield LVF viscometer being between 4000 and 10,000 cps, the molecular weight being approximately equal to 1,300,000.

More especially preferred conditioning polymers according to the invention are chosen from:
a) the poly(quaternary ammonium) polymers;
b) the copolymer of the diallyldimethylammonium chloride and acrylic acid (80/20) sold by the company CALGON under the name MERQUAT 280;
c) the homopolymer of dimethyldiallylammonium chloride sold by the company MERCK under the name MERQUAT 100;
d) the quaternized cellulose ether derivatives sold by the company UNION CARBIDE under the name JR;
e) the copolymer of vinylpyrrolidone and methacrylamidopropyltrimethylammonium chloride (85:15) sold by the company GAF under the name GAFQUAT HS 100; and
f) the cationic polymers of the ionene type sold by the company Chimex, such as hexadimethrine chloride, also known as IONENE G.

The at least one conditioning polymer is typically employed in amounts of from 0.01 to 12% by weight; from 0.1 to 10% by weight; from 0.1 to 8% by weight, all weights being based on the total weight of the composition.

The compositions of the invention may comprise at least one fatty alcohol.

As used herein, "fatty alcohol" refers to any alcohol with a carbon chain of $C_5$ or greater, such as, for example, $C_8$ or greater, $C_{10}$ or greater, and $C_{12}$ or greater. The at least one fatty alcohol may be chosen from, for example, $C_9$-$C_{11}$ alcohols, $C_{12}$-$C_{13}$ alcohols, $C_{12}$-$C_{15}$ alcohols, $C_{12}$-$C_{16}$ alcohols, $C_{14}$-$C_{15}$ alcohols, arachidyl alcohol, behenyl alcohol, caprylic alcohol, cetearyl alcohol, cetyl alcohol, coconut alcohol, decyl alcohol, hydrogenated tallow alcohol, jojoba alcohol, lauryl alcohol, myristyl alcohol, oleyl alcohol, palm alcohol, palm kernel alcohol, stearyl alcohol, tallow alcohol, and tridecyl alcohol.

As used herein, "alkoxylated fatty alcohol" refers to any fatty alcohol with a carbon chain of $C_5$ or greater, as defined above, further comprising at least one alkoxy group. For example, the at least one alkoxylated fatty alcohol may have a carbon chain of $C_8$ or greater, $C_{10}$ or greater, and $C_{12}$ or greater. Further, for example, the at least one alkoxylated fatty alcohol may be chosen from alkoxylated polymers (including co-, ter- and homo-polymers) derived from alcohols such as glycerol (e.g. polyglyceryl derived from four glycerol molecules). The at least one alkoxy group of the at least one alkoxylated fatty alcohol may, for example, be derived from an alkoxylation reaction carried out with alkylene oxide. Non-limiting examples of at least one alkoxylated fatty alcohol include any fatty alcohol comprising at least one polyethylene glycol ether and any fatty alcohol comprising at least one polypropylene glycol ether.

Non-limiting examples of the at least one alkoxylated fatty alcohol include ceteareth-2, ceteareth-3, ceteareth-4, ceteareth-5, ceteareth-6, ceteareth-7, ceteareth-8, ceteareth-9, ceteareth-10, ceteareth-11, ceteareth-12, ceteareth-13, ceteareth-14, ceteareth-15, ceteareth-16, ceteareth-17, ceteareth-18, ceteareth-20, ceteareth-22, ceteareth-23, ceteareth-24, ceteareth-25, ceteareth-27, ceteareth-28, ceteareth-29, ceteareth-30, ceterel:h-33, ceteareth-34, ceteareth-40, ceteareth-50, ceteareth-55, ceteareth-60, ceteareth-80, ceteareth-100, laureth-1, laureth-2, laureth-3, laureth-4, laureth-5, laureth-6, laureth-7, laureth-8, laureth-9, laureth-10, laureth-11, laureth-12, laureth-13, laureth-14, laureth-15, lauretih-16, laureth-20, laureth-23, laureth-25, laureth-30, laureth-40, deceth-3, deceth-5, oleth-5, oleth-30, steareth-2, steareth-10, steareth-20, steareth-100, cetylsteareth-12, ceteareth-5, ceteareth-5, polyglyceryl 4-lauryl ether, polyglyceryl 4-oleyl ether, polyglyceryl 2-oleyl ether, polyglyceryl 2-cetyl ether, polyglyceryl 6-cetyl ether, polyglyceryl 6-oleylcetyl ether, polyglyceryl 6-octadecyl ether, $C_9$-$C_{11}$ pareth-3, $C_9$-$C_{11}$ pareth-6, $C_{11}$-$C_{15}$ pareth-3, $C_{11}$-$C_{15}$ pareth-5, $C_{11}$-$C_{15}$ pareth-12, $C_{11}$-$C_{15}$ pareth-20, $C_{12}$-$C_{15}$ pareth-9, $C_{12}$-$C_{15}$ pareth-12, and $C_{22}$-$C_{24}$ pareth-33.

The fatty alcohol may be present in the composition in an amount of from 0.05 to 12% by weight, preferably from 0.1 to 10% by weight, and more preferably from 0.5 to 5% by weight, all weights being based on the total weight of the composition.

The compositions of the invention may comprise at least one surfactant.

The at least one surfactant may be selected arbitrarily, alone or as mixtures, from anionic, amphoteric, non-ionic, zwitterionic, and cationic surfactants.

The surfactants which are suitable for the implementation of certain embodiments according to the present disclosure include, for example, the following:

(i) Anionic Surfactants:

As examples of anionic surfactants which can be used, alone or as mixtures, according to the present disclosure, mention may be made of salts, such as alkali metal salts, for example sodium salts, ammonium salts, amine salts, amino alcohol salts, and magnesium salts of the following compounds: alkyl sulphates, alkyl ether sulphates, alkylamido ether sulphates, alkylaryl polyether sulphates, monoglyceride sulphates; alkylsulphonates, alkyl phosphates, alkylamidesulphonates, alkylarylsulphonates, α-olefinsulphonates, paraffinsulphonates; $(C_6$-$C_{24})$alkyl sulphosuccinates, $(C_6$-$C_{24})$ alkyl ether sulphosuccinates, $(C_6$-$C_{24})$ alkylamide sulphosuccinates; $(C_6$-$C_{24})$alkyl sulphoacetates, $(C_6$-$C_{24})$acyl sarcosinates, and $(C_6$-$C_{24})$acyl glutamates. It is also possible to use the carboxylic esters of $(C_6$-$C_{24})$alkyl polyglycosides, such as alkylglucoside citrates, alkylpolyglycoside tartrates and alkylpolyglycoside sulphosuccinates, alkylsulphosuccinamates; acyl isethionates and N-acyltaurates, the alkyl and acyl radicals of all of these various compounds for example having from 12 to 20 carbon atoms, and the aryl radicals for example being chosen from phenyl and benzyl groups. Among the anionic surfactants which can also be used, mention may also be made of fatty acid salts such as the salts of oleic, ricinoleic, palmitic, and stearic acids, coconut oil acid and hydrogenated coconut oil acid; acyl lactylates in which the acyl radicals have 8 to 20 carbon atoms. Alkyl-D-galactosideuronic acids and their salts, polyoxyalkylenated $(C_6$-$C_{24})$ alkyl ether carboxylic acids, polyoxyalkylenated $(C_6$-$C_{24})$alkyl aryl ether carboxylic acids, polyoxyalkylenated $(C_6$-$C_{24})$ alkylamido ether carboxylic acids and their salts, such as those having from 2 to 50 alkylene oxide, for example ethylene oxide groups, and mixtures thereof can also be used.

(ii) Non-Ionic Surfactants:

The non-ionic surfactants are also compounds that are well known per se. See in this respect "Handbook of Surfactants" by M. R. Porter, published by Blackie & Son (Glasgow and London), 1991, pp. 116-178. As disclosed herein, their nature may not be a critical feature. Thus, they may be selected from polyethoxylated and polypropoxylated alkylphenols, alpha-diols and alcohols having a fatty chain having, for example, 8 to 18 carbon atoms, it being possible for the number of ethylene oxide or propylene oxide groups to range from 2 to 50. Mention may also be made of copolymers of ethylene oxide and of propylene oxide, condensates of ethylene oxide and of propylene oxide with fatty alcohols; polyethoxylated fatty amides having from 2 to 30 mol of ethylene oxide, polyglycerolated fatty amides comprising on average 1 to 5, such as 1.5 to 4, glycerol groups; oxyethylenated fatty acid esters of sorbitan having from 2 to 30 mol of ethylene oxide; fatty acid esters of sucrose, fatty acid esters of polyethylene glycol, alkyl polyglycosides, N-alkylglucamine derivatives, amine oxides such as ($C_{10}$-$C_{14}$)alkylamine oxides and N-acylaminopropylmorpholine oxides. It will be noted that alkyl polyglycosides are non-ionic surfactants which should be mentioned.

(iii) Amphoteric and Zwitterionic Surfactants:

The amphoteric or zwitterionic surfactants, whose nature is not a critical feature as disclosed herein, can be chosen from aliphatic secondary and tertiary amine derivatives in which the aliphatic radical is a linear or branched chain having 8 to 18 carbon atoms and comprising at least one water-solubilizing anionic group, for example carboxylate, sulphonate, sulphate, phosphate, and phosphonate; mention may also be made of ($C_8$-$C_{20}$) alkylbetaines, sulphobetaines, ($C_8$-$C_{20}$) alkylamido($C_1$-$C_6$) alkylbetaines, and ($C_8$-$C_{20}$)alkylamido ($C_1$-$C_6$)alkylsulphobetaines. Among the amine derivatives, mention may be made of the products sold under the name MIRANOL®, as described in U.S. Pat. Nos. 2,528,378 and 2,781,354 and classified in the CTFA dictionary, 3rd edition, 1982, under the names Amphocarboxyglycinates and Amphocarboxypropionates of respective structures:

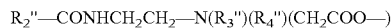

$R_2''$—$CONHCH_2CH_2$—$N(R_3'')(R_4'')(CH_2COO$—$)$ in which: $R_2''$ is chosen from linear and branched ($C_5$-$C_{20}$) alkyl radicals of, for example, an acid $R_2''$-COOH present in a group chosen from hydrolysed coconut oil, and heptyl, nonyl, and undecyl radicals, $R_3''$ denotes a beta-hydroxyethyl group, and $R_4''$ denotes a carboxymethyl group; and

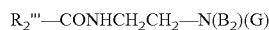

$R_2'''$—$CONHCH_2CH_2$—$N(B_2)(G)$ in which:

$B_2$ is —$CH_2CH_2OX_4$, G is —$(CH_2)_{z'}Y_4$, wherein $z'$ is chosen from 1 and 2;

$X_4$ is chosen from —$CH_2CH_2$—COOH and a hydrogen atom;

$Y_4$ is chosen from —COOH and —$CH_2$—CHOH—$SO_3H$; and $R_2'''$ is chosen from linear and branched, saturated and unsaturated, ($C_5$-$C_{20}$) alkyl radicals of an acid $R_2'''$—COOH present, for example, in coconut oil or in hydrolysed linseed oil, alkyl radicals, such as $C_7$, $C_9$, $C_{11}$, and $C_{13}$ alkyl radicals, $C_{17}$ alkyl radicals and its iso form, and unsaturated $C_{17}$ radicals.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Capryloamphodipropionate, Lauroamphodipropionic acid, and Cocoamphodipropionic acid.

By way of example, mention may be made of the cocoamphodiacetate sold under the trade name MIRANOL® C2M concentrate by the company Rhodia Chimie.

(iv) Cationic Surfactants:

Among the cationic surfactants, mention may be made of: primary, secondary, and tertiary fatty amine salts, optionally polyoxyalkylenated; quaternary ammonium salts such as tetraalkylammonium, alkylamidoalkyltrialkylammonium, trialkylbenzylammonium, trialkylhydroxyalkylammonium and alkylpyridinium chlorides or bromides; imidazoline derivatives; and cationic amine oxides.

The amounts of surfactants present in the compositions disclosed herein may range from 0.01% to 40%, such as from 0.5% to 30% by weight relative to the total weight of the composition.

The compositions disclosed herein may further comprise at least one rheology modifier such as cellulosic thickeners, for example hydroxyethylcellulose, hydroxypropylcellulose, and carboxymethylcellulose, guar gum and its derivatives, such as hydroxypropylguar, gums of microbial origin, such as xanthan gum and scleroglucan gum, and synthetic thickeners such as crosslinked homopolymers of acrylic acid and of acrylamidopropanesulphonic acid.

The supplementary thickener may be present in an amount ranging from 0.01% to 10% by weight relative to the total weight of the composition.

The medium of the composition, which is suitable for dyeing, may be an aqueous medium comprising water and may comprise at least one cosmetically acceptable organic solvent such as, for example, alcohols such as ethyl alcohol, isopropyl alcohol, benzyl alcohol and phenylethyl alcohol, and polyols and polyol ethers such as, for example, ethylene glycol monomethyl, monoethyl and monobutyl ether, propylene glycol and its ethers such as, for example, propylene glycol monomethyl ether, butylene glycol, dipropylene glycol, and also diethylene glycol alkyl ethers such as, for example, diethylene glycol monoethyl ether and monobutyl ether.

The at least one solvent may then be present in concentrations ranging from 0.5% to 20%, such as from 2% to 10% by weight, relative to the total weight of the composition.

The composition (A) may also comprise an effective amount of at least one additional agent, known previously elsewhere in oxidation dyeing, such as various common adjuvants, for instance sequestrants such as EDTA and etidronic acid, UV screening agents, waxes, volatile or non-volatile, cyclic, linear or branched silicones, which are optionally organically modified (in particular with amine groups), preservatives, ceramides, pseudoceramides, vegetable, mineral oils, synthetic oils, vitamins, and provitamins, for instance panthenol.

The said composition may also comprise at least one of reducing agents and antioxidants. These agents may be chosen from sodium sulphite, thioglycolic acid, thiolactic acid, sodium bisulphite, dehydroascorbic acid, hydroquinone, 2-methylhydro-quinone, tert-butylhydroquinone and homogentisic acid, and, in this case, they are generally present in amounts ranging from 0.05% to 1.5% by weight relative to the total weight of the composition.

Needless to say, a person skilled in the art will take care to select the optional additional compound(s) mentioned above such that the advantageous properties intrinsically associated with the dye composition disclosed herein are not, or are not substantially, adversely affected by the envisaged addition(s).

In the ready-to-use composition or in the composition (B), the oxidizing agent may be chosen from urea peroxide, alkali metal bromates, and ferricyanides, and persalts such as perborates and persulphates. In one embodiment, hydrogen peroxide may be used. This oxidizing agent advantageously comprises an aqueous hydrogen peroxide solution whose titre may range from 1 to 40 volumes, such as from 5 to 40 volumes.

Oxidizing agents that may also be used include at least one redox enzyme such as laccases, peroxidases, and 2-electron oxidoreductases, such as uricase, where appropriate in the presence of their respective donor or co-factor.

The pH of the ready-to-use composition applied to the keratin fibers, i.e., the composition resulting from mixing together the dye composition (A) and the oxidizing composition (B), may range from 4 to 11, such as from 6 to 10, and it may be adjusted to the desired value using acidifying or basifying agents that are well known in the art in the dyeing of keratin fibers.

Among the basifying agents which may be mentioned, for example, are aqueous ammonia, alkali metal carbonates, alkanolamines such as monoethanolamine, diethanolamine and triethanolamine and derivatives thereof, oxyethylenated and oxypropylenated hydroxyalkylamines and ethylenediamines, sodium hydroxide and potassium hydroxide.

The acidifying agents are chosen from, for example, mineral and organic acids, for instance hydrochloric acid, orthophosphoric acid, carboxylic acids, for instance tartaric acid, citric acid, lactic acid, and sulphonic acids.

The dyeing process disclosed herein may comprise applying the ready-to-use composition, prepared at the time of use from the compositions (A) and (B) described above, to wet or damp keratin fibers, and in leaving the composition to act for a waiting time ranging from 1 to 60 minutes, such as from 10 to 45 minutes, in rinsing the fibers and then in optionally washing the fibers with shampoo, then rinsing them again and drying them.

One variant of this process comprises applying an above-described composition and a composition comprising at least one oxidizing agent sequentially with a time delay or simultaneously to wet or damp keratin fibers, with an optional intermediate rinse, and in leaving the said compositions to act for an exposure time ranging from 1 to 60 minutes and then in rinsing the fibers, and then optionally in washing the fibers with shampoo, then rinsing them again and drying them.

The present invention will be better understood from the Examples which follow, all of which are intended for illustrative purposes only, and are not meant to unduly limit the scope of the invention in any way.

EXAMPLE

All dyeing compositions presented in the examples were mixed with an oxidizing composition corresponding to the following formula, prior to their application onto hair or swatches of hair:

Oxidizing Composition:

|  | % by weight |
| --- | --- |
| Fatty alcohol | 2.3 |
| Oxyethylenated fatty alcohol | 0.6 |
| Fatty amide | 0.9 |
| Glycerin | 0.5 |
| Hydrogen peroxide | 7.5 |
| Perfume | QS |
| Demineralized water | QS to 100 |

Dyeing Compositions:

| Ingredients | Formula A, % by weight | Formula B, % by weight | Formula C, % by weight |
| --- | --- | --- | --- |
| Fatty acid alkanolamide | 23.7 | — | 23.7 |
| Polyquaternium-6 | 0.8 | — | — |
| Polyquaternium-22 | — | 1.22 | — |
| Hexadimethrine chloride | 1.2 | 2.4 | — |
| Cetrimonium chloride | — | — | 2.0 |
| Dilinoleic acid | 5.0 | — | 5.0 |
| Glycerin | 3.0 | — | 3.0 |
| C3-C6 Glycol | 0.54 | 7 | 0.54 |
| Oxyethylenated fatty acid amine | 3.0 | — | 3.0 |
| Fatty alcohol | 1.84 | 11.5 | 1.84 |
| Fatty acid | 0.08 | 3.0 | 0.08 |
| Oxidative dye precursors | 1.7 | 1.7 | 1.7 |
| Ammonium hydroxide | QS | QS | QS |
| Neutralizing agent | QS | QS | QS |
| Reducing agents | QS | QS | QS |
| Sequestering agent | QS | QS | QS |
| Fragrance | QS | QS | QS |
| Other cosmetic additives | QS | QS | QS |
| Water | QS to 100 | QS to 100 | QS to 100 |

Each dyeing composition was mixed, at the time of use, in a plastic bowl and for 2 minutes, with the oxidizing composition given above, in an amount of 1 part of dyeing composition per 1 part of oxidizing composition. The mixture obtained was applied to swatches of 3 grams of permed and unpermed natural grey hair which is 90% white and allowed to act for 30 minutes in a bath ratio: 10 g of mixture per 1 g of hair and were laid out flat on a support.

The swatches were then rinsed with water, they were washed with shampoo and again rinsed with water, and then dried and disentangled.

Example 1

Colorimetric Test on Use of Fatty Amides

The color of the dye-treated swatches was measured using a Minolta CM2002 colorimeter in the L*a*b* system. In the L*a*b* system, the 3 parameters denote, respectively, the intensity (L*), the shade (a*) and the saturation (b*).

According to this system, the greater the value of L, the lighter or less intense the color. Conversely, the lower the value of L, the darker or more intense the color.

The ΔL or the difference between the L value for the dye-treated hair versus the L value for the control hair sample represents a change in the value of L: the more negative the ΔL value is, the darker the color that is deposited on the hair. ΔL=$L_t$ (dye-treated hair)–$L_c$ (control, 90% grey hair)

The results are collated in Table (1) below:

Colorimetric measurements (average of 24 measurements along the length of each swatch)

|  | $L_c$ control, 90% grey hair | $L_t$ Dye-treated hair | $\Delta L$ Difference in L values between dye-treated hair and control |
|---|---|---|---|
| Formula A (on unpermed hair) | 61.55 | 42.37 | −19.18 |
| Formula B (on unpermed hair) | 61.55 | 45.75 | −15.80 |
| Formula A (on permed hair) | 63.12 | 36.55 | −26.57 |
| Formula B (on permed hair) | 63.12 | 40.84 | −22.28 |

Conclusion: The $\Delta L$ values for Formula A for both unpermed and permed hair were more negative compared to those for Formula B for both unpermed and permed hair, which indicated that more color was deposited on the hair treated with Formula A which contained the fatty amides.

Example 2

Evaluation of Conditioning Properties on Use of Conditioning Polymers Versus Conditioning Non-polymeric Agents The dyeing compositions, Formula A and Formula C, were applied to swatches of 3 grams of unpermed natural grey hair which is 90% white. Three complete application cycles of dye treatment, then shampoo, were performed on each swatch sample.

The swatches were evaluated for conditioning properties by a panel of 10 expert evaluators. The hair treated with Formula A above, which contained the conditioning polymers, was rated by 8 out of the 10 expert evaluators as being smoother and softer than hair treated with Formula C, which was considered rough-feeling.

Example 3

Colorimetric Test on Use of Dilinoleic Acid

Dyeing Compositions: Formulas D and E contained 5% and 7.5% dilinoleic acid, respectively, Formula F did not contain dilinoleic acid and Formula G contained oleic acid instead of the diacid.

| Ingredients | Formula D, % by weight | Formula E, % by weight | Formula F, % by weight | Formula G, % by weight |
|---|---|---|---|---|
| Fatty acid alkanolamide | 23.7 | 23.7 | 23.7 | 23.7 |
| Polyquaternium-6 | 0.8 | 0.8 | 0.8 | 0.8 |
| Hexadimethrine chloride | 1.2 | 1.2 | 1.2 | 1.2 |
| Dilinoleic Acid | 5.0 | 7.5 | — | — |
| Oleic acid | — | — | — | 10 |
| Glycerin | 3.0 | 3.0 | 3.0 | 3.0 |
| C3-C6 Glycol | 0.54 | 0.54 | 0.54 | 0.54 |
| Oxyethylenated fatty acid amine | 3.0 | 3.0 | 3.0 | 3.0 |
| Fatty alcohol | 1.84 | 1.84 | 1.84 | 1.84 |
| Fatty acid | 0.08 | 0.08 | 0.08 | 0.08 |
| Oxidative dye precursors | 1.7 | 1.7 | 1.7 | 1.7 |
| Ammonium hydroxide | QS | QS | QS | QS |
| Neutralizing agent | QS | QS | QS | QS |
| Reducing agents | QS | QS | QS | QS |
| Sequestering agent | QS | QS | QS | QS |
| Fragrance | QS | QS | QS | QS |
| Other cosmetic additives | QS | QS | QS | QS |
| Water | QS to 100 | QS to 100 | QS to 100 | QS to 100 |

The colorimetric measurements were conducted on unpermed hair according to the procedure described in Example 1. The results are collated in Table (2) below:

Colorimetric measurements (average of 24 measurements along the length of each swatch)

|  | $L_c$ control, 90% grey hair | $L_t$ Dye-treated hair | $\Delta L$ Difference in L values between dye-treated hair and control |
|---|---|---|---|
| Formula D (on unpermed hair) | 63.94 | 29.77 | −34.18 |
| Formula E (on unpermed hair) | 63.94 | 29.72 | −34.23 |
| Formula F (on unpermed hair) | 63.94 | 32.64 | −31.30 |
| Formula G (on unpermed hair) | 63.94 | 31.37 | −32.57 |

Conclusion: The $\Delta L$ values for Formulas D and E were both more negative compared to those for Formulas F and G, which indicated that more color was deposited on the hair treated with Formulas D and E which contained dilinoleic acid.

What is claimed is:

1. A dyeing composition comprising:
   (a) greater than about 10% by weight, based on the weight of the composition, of at least one fatty acid alkanolamide;
   (b) at least one $C_6$-$C_{36}$ dicarboxylic acid;
   (c) at least one water soluble base capable of reacting with (b) to form a soap;
   (d) at least one conditioning polymer; and
   (e) at least one oxidation dye, and wherein the composition is in cream form.

2. The composition of claim 1 wherein the at least one fatty acid alkanolamide is chosen from coco monoethanolamide, stearic acid monoethanolamide, and mixtures thereof.

3. The composition of claim 1 wherein (a) is present in the composition in an amount of greater than about 15% by weight, based on the weight of the composition.

4. The composition of claim 1 wherein (a) is present in the composition in an amount of greater than about 20% by weight, based on the weight of the composition.

5. The composition of claim 1 wherein (b) is present in the composition in an amount of from about 0.1 to about 15% by weight, based on the weight of the composition.

6. The composition of claim 1 wherein (b) is present in the composition in an amount of from about 0.5 to about 12% by weight, based on the weight of the composition.

7. The composition of claim 1 wherein (b) is dilinoleic acid.

8. The composition of claim 1 wherein (c) is chosen from monoethanolamines, diethanolamines, triethanolamines, and mixtures thereof.

9. The composition of claim 1 wherein (c) is present in the composition in an amount of from about 0.01 to about 5% by weight, based on the weight of the composition.

10. The composition of claim 1 wherein (c) is present in the composition in an amount of from about 0.1 to about 3% by weight, based on the weight of the composition.

11. The composition of claim 1 wherein (d) is an ionene-type cationic polymer.

12. The composition of claim 1 wherein (d) is present in the composition in an amount of from about 0.1 to about 12% by weight, based on the weight of the composition.

13. The composition of claim 1 wherein (d) is present in the composition in an amount of from about 0.1 to about 10% by weight, based on the weight of the composition.

14. The composition of claim 1 further comprising at least one oxidizing agent.

15. A process for dyeing hair comprising contacting the hair with a composition containing:
 (a) greater than about 10% by weight, based on the weight of the composition, of at least one fatty acid alkanolamide;
 (b) at least one $C_6$-$C_{36}$ dicarboxylic acid;
 (c) at least one water soluble base capable of reacting with (b) to form a soap;
 (d) at least one conditioning polymer;
 (e) at least one oxidation dye; and
 (f) at least one oxidizing agent,
 and wherein the composition is in cream form.

16. The process of claim 15 wherein the at least one fatty acid alkanolamide is chosen from coco monoethanolamide, stearic acid monoethanolamide, and mixtures thereof.

17. The process of claim 15 wherein (a) is present in the composition in an amount of greater than about 15% by weight, based on the weight of the composition.

18. The process of claim 15 wherein (a) is present in the composition in an amount of greater than about 20% by weight, based on the weight of the composition.

19. The process of claim 15 wherein (b) is present in the composition in an amount of from about 0.1 to about 15% by weight, based on the weight of the composition.

20. The process of claim 15 wherein (b) is present in the composition in an amount of from about 0.5 to about 12% by weight, based on the weight of the composition.

21. The process of claim 15 wherein (b) is dilinoleic acid.

22. The process of claim 15 wherein (c) is chosen from monoethanolamines, diethanolamines, triethanolamines, and mixtures thereof.

23. The process of claim 15 wherein (c) is present in the composition in an amount of from about 0.01 to about 5% by weight, based on the weight of the composition.

24. The process of claim 15 wherein (c) is present in the composition in an amount of from about 0.1 to about 3% by weight, based on the weight of the composition.

25. The process of claim 15 wherein (d) is an ionene-type cationic polymer.

26. The process of claim 15 wherein (d) is present in the composition in an amount of from about 0.1 to about 12% by weight, based on the weight of the composition.

27. The process of claim 15 wherein (d) is present in the composition in an amount of from about 0.1 to about 10% by weight, based on the weight of the composition.

* * * * *